United States Patent
Kross et al.

[11] Patent Number: 6,120,731
[45] Date of Patent: Sep. 19, 2000

[54] FROZEN CHLORINE DIOXIDE-CONTAINING COMPOSITION AND METHODS RELATED THERETO

[75] Inventors: Robert D. Kross, Bellmore, N.Y.; G. Kere Kemp, Mercer Island, Wash.

[73] Assignee: Alcide Corporation, Redmond, Wash.

[21] Appl. No.: 09/251,980

[22] Filed: Feb. 18, 1999

[51] Int. Cl.[7] .......................... A01N 25/08; A23L 3/3409; A23L 3/3454; C01B 11/02
[52] U.S. Cl. ................................. 422/29; 422/37; 422/40; 252/187.21; 252/187.23; 424/409; 424/44; 426/67; 426/320; 426/327; 426/331; 426/332; 426/335
[58] Field of Search ........................ 252/187.21, 187.23; 422/28, 29, 37, 40; 424/405, 409, 44, 661; 426/66, 67, 68, 320, 327, 331, 332, 333, 335

[56] References Cited

U.S. PATENT DOCUMENTS

| | | | |
|---|---|---|---|
| 4,021,585 | 5/1977 | Svoboda et al. | 426/332 |
| 4,832,972 | 5/1989 | Toledo-Flores et al. | 426/327 |
| 5,116,620 | 5/1992 | Chvapil et al. | 424/445 |
| 5,152,912 | 10/1992 | Dziabo et al. | 514/840 |
| 5,185,161 | 2/1993 | Davidson et al. | 424/665 |
| 5,279,673 | 1/1994 | Dziabo et al. | 514/840 |

OTHER PUBLICATIONS

JP Abstract No. 07315804 A.
JP Abstract No. 62215377 A.
Derwent Abstract ACC–No. 1985–114264.
Bio–cide International, Inc. Food Adbitive Petition, 6A4499 Filed May 8, 1996).

*Primary Examiner*—Joseph D. Anthony
*Attorney, Agent, or Firm*—Seed Intellectual Property Law Group PLLC

[57] ABSTRACT

A frozen chlorine dioxide-containing composition comprising a metal chlorite and a protic acid in a frozen aqueous matrix made by freezing a substantially chlorine dioxide-free aqueous solution comprising a metal chlorite at a concentration ranging from about 0.0005% to about 0.5% by weight and a protic acid at a concentration sufficient to lower the pH of the aqueous solution to a value of about 1.8 to about 5.0. The frozen chlorine dioxide-containing composition has a chlorine dioxide concentration of more than about 3 ppm, while the aqueous solution prior to freezing has a chlorine dioxide concentration less than about 3 ppm. The frozen chlorine dioxide-containing composition is used to disinfect substrates by contacting the same with the frozen chlorine dioxide-containing composition. Suitable substrates include food intended for human or animal consumption, such as meat, fish and poultry.

30 Claims, No Drawings

FROZEN CHLORINE DIOXIDE-CONTAINING COMPOSITION AND METHODS RELATED THERETO

TECHNICAL FIELD

The present invention relates to a frozen chlorine dioxide-containing composition comprising a metal chlorite and a protic acid in a frozen aqueous matrix, and to methods of making the same by freezing an aqueous solution comprising a metal chlorite and a protic acid, as well as to methods of disinfecting a substrate by contacting the substrate with the frozen chlorine dioxide-containing composition.

BACKGROUND OF THE INVENTION

The generation and use of chlorine dioxide for disinfection purposes, bleaching, and related oxidative tasks, has been disclosed in the technical literature as well as in an extensive series of patents. In general, for large scale usage, chlorine dioxide has been directly created by oxidation or acidification of chlorite, and/or by reduction of chlorate. When chlorite is acidified, the resulting chlorous acid (hydrogen chlorite) is an unstable species that decomposes to form the higher-valent chlorine dioxide gas and chlorate, and the lower-valent chloride ion. At lower concentrations of either or both reactants, the transformation is much less rapid. Thus, commercial production of chlorine dioxide gas is generally effected with higher reactant levels.

There have been many unique approaches to the generation of chlorine dioxide under specialized circumstances. Examples of these can be found in U.S. Pat. No. 4,104,190 wherein chlorite is oxidized by a chlorine source; in U.S. Pat. Nos. 4,689,169 and 5,399,288 wherein chlorine dioxide is generated from dry compositions; in U.S. Pat. Nos. 4,731,193 and 4,861,514 wherein chlorine dioxide is generated in thickened media for extended activity; and in U.S. Pat. Nos. 5,104,660 and 5,126,070 wherein chlorine dioxide is created by rupture or addition of moisture to dry precursors in enclosed compartments. Other approaches for generating chlorine dioxide include formation from concentrated reactants as disclosed in U.S. Pat. Nos. 3,386,915 and 4,925,645 and Canadian Patent No. 959,258; triggering chlorite with transition elements as disclosed in U.S. Pat. No. 5,008,096; and interaction of adsorbed precursors impregnated into zeolites as disclosed in U.S. Pat. Nos. 5,567,405 and 5,573,743. Additional means of providing chlorine dioxide, such as disclosed in U.S. Pat. Nos. 3,123,521 and 3,271,242, are by acidification or dilution of so-called "stabilized chlorine dioxide solutions." Such solutions, however, are in reality stabilized chlorite solutions, since small amounts of chlorine dioxide that are slowly created in chlorite solutions are continuously reduced back to the chlorite form by peroxy compounds.

Other disclosures have dealt with the use of chlorine dioxide for specific disinfection purposes. These include U.S. Pat. No. 4,021,585 disclosing a low-concentration chlorine dioxide spray for meat disinfection; U.S. Pat. No. 4,504,442 teaching the use of chlorine dioxide gas to disinfect impermeable surfaces; U.S. Pat. No. 5,116,620 for disinfecting wounds; and U.S. Pat. Nos. 5,152,912 and 5,279,673 for disinfecting contact lenses. Chlorine dioxide was also one of several means used to disinfect fish, as part of a patented sequential process for preserving its quality, which involves disinfection, supercooling, and sub-zero, non-frozen storage of the fish, as disclosed in U.S. Pat. No. 4,832,972.

Bacterial attack on fresh food items of commerce has long been a problem. Between the time of harvesting agricultural commodities, or catching fish and/or shellfish on ocean-going vessels, or transporting freshly-killed poultry, and the like, and/or retail storage of these food materials, and the customer's purchase of these foods, pathogenic and spoilage bacteria continue to multiply exponentially. Cooler temperatures tend to suppress this growth. In many operations ice and refrigeration have been used to retard such spoilage, as was disclosed in the process described for extending the shelf life of fish in U.S. Pat. No. 4,832,972. In addition, many freshly-collected food items can be subjected to initial disinfecting sprays, such as with chlorinated water, sorbates or organic acids.

A recent Food Additive Petition has been made to the U.S. Food & Drug Administration, in which the commercial use of ice containing chlorine dioxide has been requested (Bio-Cide International, Inc., Food Additive Petition 6A4499, filed May 8, 1996). The preparation of such ice is somewhat tedious, and potentially dangerous with respect to the inhalation of high levels of chlorine dioxide from the initial concentrates. These concentrates are prepared, for example, from a combination of 10% citric acid and 2.0% aqueous sodium chlorite solution, which results in upwards of 5,000 parts per million (ppm) of chlorine dioxide in the solution. The solution is then diluted with water so that the final concentration of chlorine dioxide plus sodium chlorite is no more than about 25 ppm, which liquid is then frozen. Since the permitted level for continuous exposure of factory workers to chlorine dioxide is only 0.1 ppm in the air, and since chlorine dioxide is a volatile gas, such preparation and use is potentially problematic, as well as expensive.

However, one of the advantages of chlorine dioxide is that, as a gas, it can escape from frozen or re-liquefied water and permeate the surfaces of food to reduce their microbial loading. To this end, the use of chlorine dioxide-impregnated ice would be particularly advantageous for the storage of fish and shellfish after harvesting. Fish, particularly in tropical areas, can spoil within hours at ambient temperatures because bacteria on their surfaces multiply rapidly and invade the tissues. The putrefaction that results from such proliferation, as well as degradative biochemical processes, could well be suppressed by the use of ice containing chlorine dioxide. However, the large quantities of ice that would be needed would be prohibitively expensive if prepared by the activation/dilution process that is currently under development.

Accordingly, there is a need in the art for simpler and more cost-efficient techniques for producing chlorine dioxide-containing ice, as well as the use of such ice to disinfect a variety of substrates, particularly food. The present invention fulfills these needs, and provides other related advantages.

SUMMARY OF THE INVENTION

In brief, the present invention is directed to a frozen chlorine dioxide-containing composition, comprising a metal chlorite and a protic acid in a frozen aqueous matrix. The frozen chlorine dioxide-containing composition has a chlorine dioxide concentration of more than about 3 ppm chlorine dioxide, generally in the range of 3 to 200 ppm, and typically in the range of 5 to 100 ppm. The precise amount will depend upon (and be optimized for) the intended use of the frozen chlorine dioxide-containing composition. The composition prior to freezing is an aqueous solution comprising a metal chlorite at a concentration ranging from about 0.0005% to about 0.5% by weight, and a protic acid at a concentration sufficient to lower the pH of the aqueous solution to a value of about 1.8 to about 5.0. Furthermore, the aqueous solution prior to freezing has a chlorine dioxide concentration less than about 3 ppm.

In more specific embodiments, the metal chlorite is an alkali or alkaline earth chlorite, such as sodium chlorite or potassium chlorite. The metal chlorite may be present at a concentration ranging from 0.001% to 0.25% by weight, and typically from 0.0025% to 0.125% by weight. The protic acid may be an organic acid, such as tartaric, citric, malic, and acetic, or may be an inorganic acid, such as phosphoric acid, or may be any combination thereof. The protic acid may be present in the aqueous solution at a concentration sufficient to lower the pH of the aqueous solution to a value from 2.0 to 4.0, and typically from 2.5 to 3.5. The aqueous solution, prior to freezing, may have a chlorine dioxide concentration less than 2 ppm, or less than 1 ppm, or may contain no detectable levels of chlorine dioxide. The aqueous solution may be formed in a variety of ways, including mixing of an aqueous solution of protic acid and an aqueous solution of metal chlorite, a protic acid in solid form and an aqueous solution of metal chlorite, an aqueous solution of protic acid and a metal chlorite in dry form, or a protic acid in dry form and a metal chlorite in dry form followed by addition of water.

In another embodiment, a method is disclosed for disinfecting a substrate comprising contacting the substrate with the frozen chlorine dioxide-containing composition of this invention. The substrate may be food intended for human or animal consumption, including fruit, vegetables and meat products, such as beef, fish or poultry. Substrates also include medical products, animal organs, or any other tissue, material or substance which would benefit by contact with the frozen chlorine dioxide-containing composition of this invention. In one aspect of this embodiment, the method further comprises the step of contacting the frozen chlorine dioxide-containing composition with a chloride ion. Suitable sources for chloride ions in this context include seawater and brine.

In still a further embodiment, a method for making a frozen chlorine dioxide-containing composition is disclosed, wherein the method involves freezing an aqueous solution which, prior to freezing, comprises a metal chlorite at a concentration ranging from about 0.0005% to about 0.5% by weight and a protic acid at a concentration sufficient to lower the pH of the aqueous solution to a value of about 1.8 to about 5.0. The resulting frozen chlorine dioxide-containing composition has a chlorine dioxide concentration of more than about 3 ppm chlorine dioxide, while the aqueous solution prior to freezing has a chlorine dioxide concentration of less than about 3 ppm.

These and other aspects of this invention will be evident upon reference to the following detailed description.

DETAILED DESCRIPTION OF THE INVENTION

As noted above, the present invention is generally directed to a frozen chlorine dioxide-containing composition comprising a metal chlorite and a protic acid in a frozen aqueous matrix, and to methods of making the same by freezing an aqueous solution comprising a metal chlorite and a protic acid, as well as to methods of disinfecting a substrate by contacting the substrate with the frozen chlorine dioxide-containing composition. The frozen chlorine dioxide-containing composition, also referred to herein as chlorine dioxide-containing ice or "CDC ice," is made from dilute acidic chlorite solutions, which thus avoids the initial cumbersome and hazardous preparation of an aqueous chlorine dioxide concentrate solution followed by dilution and a subsequent freezing step. In addition, when the substrate to be disinfected is, for example, marine fish or shellfish, the sea salt remaining on the fish or shellfish results in the enhanced generation of chlorine dioxide from the acidified chlorite matrix of the frozen chlorine dioxide-containing composition, which aids in disinfection.

The present invention provides, in one aspect, an aqueous composition which, prior to freezing, contains minimum concentrations of chlorine dioxide in the liquid state, but which, upon freezing, generates substantial quantities of chlorine dioxide. The chlorine dioxide is then released by diffusion through the frozen matrix of the frozen chlorine dioxide-containing composition and disinfects any substrate in contact or close proximity therewith. In addition, upon thawing, the resulting liquid solution releases chlorine dioxide and provides further microbiocidal action. In another aspect, the frozen chlorine dioxide-containing composition containing the newly-generated chlorine dioxide will, upon contact with chloride ions, generate further levels of chlorine dioxide which can more effectively destroy microorganisms.

Accordingly, the present invention relates to new chlorine dioxide-containing compositions, and methods for their use. More particularly, the invention relates to the creation of enhanced levels of chlorine dioxide by freezing low-concentration acidified sodium chlorite solutions which would otherwise have minimum tendency to form chlorine dioxide. In one embodiment of the invention, the chlorine dioxide-containing composition, upon contact with brine, or other aqueous chloride-bearing solutions, creates further amounts of chlorine dioxide in the aqueous ice/brine environment. The resulting composition ice can effectively serve to disinfect food items with which it is in contact, and most effectively those items such as seafood which have salt water on their surfaces.

The frozen chlorine dioxide-containing composition of this invention is formed by freezing an aqueous solution of acidified sodium chlorite at concentrations and pH's where the solution has a low, and slow tendency to form chlorine dioxide. It is known that the acidification of chlorite solutions brings about the release of chlorine dioxide, which evolution is favored by high concentrations of chlorite and/or hydrogen ion. The acidification of chlorite ion causes the corresponding, unstable hydrogen chlorite (chlorous acid) to form (i.e. $ClO_2^- + H^+ \rightarrow HClO_2$). Chlorous acid in turn degrades in an exponential and complex manner to form other-valent chlorine species, primarily chloride ion ($Cl^-$), chlorate ion ($ClO_3^+$) and chlorine dioxide gas ($ClO_2$). The concentration effects which drive this reaction to greater yields of $ClO_2$ can be noted from the following empirical reaction-rate equation, a simplified form of the more-complex equation which applies when substantial chloride ion is present in the aqueous medium.

$$\frac{d[HClO_2]}{dt} = k_1[HClO_2]^2 + k_2[HClO_2][ClO_2^-]$$

where $k_1$ and $k_2$ are rate constants. Indeed, a major source of chlorine dioxide for disinfection, bleaching, or other oxidizing functions has historically been made from acidified chlorite solutions. $ClO_2$ has found major application in potable water disinfection and in the pulp and paper industry, and in more recent times for the disinfection of foods and food-disinfecting equipment. In the last few years, aqueous $ClO_2$ concentrates have been prepared from high acid/chlorite compositions, and those concentrates then diluted and frozen to form a disinfecting ice (See Bio-Cide Food Additive Petition, supra). Since $ClO_2$ is a noxious gas, this two-step approach is potentially harmful to prepare, as well as cumbersome and expensive to carry out.

Davidson et al., in U.S. Pat. Nos. 4,986,990 and 5,185,161, showed that chlorous acid itself can be tapped as a source of antimicrobial activity by creating a low acid, low chlorite environment in which chlorous acid may be maintained in a metastable state. This is achieved in an acid/chlorite medium where the relative molar amount of chlorite that exists in the chlorous acid form is less than about 15% of the total moles of chlorite. Under such conditions, it is possible to have chlorous acid in aqueous solution without appreciable disproportionation to $ClO_2$ and chloride and chlorate ions. The favorable concentrations of chlorite for such metastability are below about 0.45%, as metal chlorite, and an acid concentration such that the pH of the solution is equal or greater than 2.7. It has been recognized in working with such solutions, at reduced temperatures (but above freezing), that the rate at which $ClO_2$ forms in these solutions is dramatically reduced as the temperature is increasing lowered towards the freezing point. This, of course, is consistent with the known laws of chemistry, where decreased temperatures slow down the interaction of reactants, in both the liquid and gaseous states.

However, in experiments with low concentration, low $ClO_2$-generating acid/chlorite solutions, in which these mixtures were cooled to below the freezing point, an unexpected formation of high levels of $ClO_2$ has been found. This is apparent in the resulting ice, which develops a yellow-green color and from which the strong odor characteristic of $ClO_2$ emanates. For example, solutions that contained from 500 to 1200 ppm of sodium chlorite (0.05%–0.12%) and that were acidified to pH 3.0 with citric acid, had the $ClO_2$ levels noted below in Table 1 before and after freezing. (The levels in the ice were determined by melting a known weight of ice in a known quantity of water, measuring the $ClO_2$ in the solution spectrophotometrically, and adjusting back to the pure ice basis.)

TABLE 1

| Sodium Chlorite Conc'n* | $ClO_2$ in Solution | $ClO_2$ in Ice |
|---|---|---|
| parts per million (ppm) | | |
| 500 | 1.4 | 56.1 |
| 850 | 1.9 | 59.5 |
| 1200 | 2.4 | 68.4 |

*at pH = 3.0

It is believed that this unexpected formation of $ClO_2$ to levels ~30–40 times greater than in the solution immediately pre-freezing, comes about because the water in the solution tends to freeze in pure form, excluding solutes. Therefore, as freezing proceeds, the chlorite and acid concentrations in the liquid phase continuously increase to the point of sufficiently high relative chlorous acid levels that disproportionation is accelerated, even at temperatures ~0° C. While the disproportionation is minimized down to 0° C., in the liquid state, it is rapidly increased at ~0° C. in the ice-forming matrix.

A further discovery regarding the chlorine dioxide-containing ice was that, upon contacting with a brine solution which approximated the composition of seawater (3.25% sodium chloride), the ice compositions generated further levels of $ClO_2$ in the surrounding brine. The additional quantity of $ClO_2$ created was determined, on the basis of the original ice quantity, by adding a known amount of the chlorine dioxide-containing ice to a known quantity of saline, quantifying the $ClO_2$ spectrometrically upon full melting, and relating the $ClO_2$ back to the original ice. While the original ice did not contain that high a level of $ClO_2$, it nonetheless caused it to be created upon contact with the saline. The following Table 2 compares the $ClO_2$ already present in the ice with that formed upon saline contact, expressed on the basis of the original chlorine dioxide-containing ice.

TABLE 2

| | $ClO_2$ in and/or formed by ice | | | | |
|---|---|---|---|---|---|
| Sodium Chlorite Conc'n* | $ClO_2$ in Solution | Water Diluent | Saline Diluent | Increase | % |
| parts per million (ppm) | | | | | |
| 500 | 1.4 | 56.1 | 112 | 56 | 100 |
| 850 | 1.9 | 59.5 | 201 | 141 | 237 |
| 1200 | 2.4 | 68.4 | 266 | 198 | 289 |

*at pH = 3.0

A similar study was performed with the same concentrations of sodium chlorite, with the solution pH adjusted to 3.5 using citric acid. The level of formation of $ClO_2$ in the ice was significantly less, and there was no enhanced creation of $ClO_2$ upon contact of the ice with brine solution (see Table 3).

TABLE 3

| | $ClO_2$ in and/or formed by ice | | | | |
|---|---|---|---|---|---|
| Sodium Chlorite Conc'n* | $ClO_2$ in Solution | Water Diluent | Saline Diluent | Increase | % |
| parts per million (ppm) | | | | | |
| 500 | <0.1 | 13.5 | 13.5 | — | ns** |
| 850 | <0.1 | 13.1 | 13.8 | — | ns** |
| 1200 | <0.1 | 13.8 | 14.5 | — | ns** |

*at pH = 3.5, prepared from cold premixes
**ns = not significantly different

It is believed that the lower generation of $ClO_2$ upon freezing a pH 3.5 sodium chlorite solution vs. a pH 3.0 solution is due to the lower relative molar amount, at pH 3.5, of chlorous acid with respect to total chlorite, ~2.8%, while at pH 3.0 the relative chlorous acid level is ~8.5%, or about 3-times higher. It is further believed that the complex relationship between the chloride ion's effect on the rate of chlorous acid disproportionation and chlorous acid concentration is such that, when the chlorous acid falls below about 3% relative to total chlorite moles (i.e., ~pH 3.5), the chloride ion's presence in the solution has little catalytic impact on chlorous acid degradation.

This invention, therefore, provides a means of preparing an antimicrobial chlorine dioxide-containing ice for the cold storage and/or transport and concomitant disinfection of foods and/or other materials (collectively referred to herein as "substrates") where the presence and proliferation of surface microorganisms would be detrimental to its quality. This would apply to a variety of fruits and vegetables, as well as animal products such as meats, fish and poultry products. It may also serve an effective function in the transport of medical products that require refrigeration, such as transplantable organs which must remain sterile. An enhanced benefit may be obtained when the antimicrobial, chlorine dioxide-containing ice is used for the storage and transport of marine fish and shellfish, which have residual seawater associated with them. The chloride ion in the water, averaging ~3.25% as sodium chloride, is an effective catalyst for the rapid degradation of chlorous acid embodied in the frozen solution of acidified sodium chlorite. The more rapid the disproportionation of the chlorous acid, the greater the relative yield of $ClO_2$ with respect to the other end products, chloride and chlorate ions.

With respect to the levels of $ClO_2$ and chlorine dioxide-containing ice required for effective disinfection of a substrate in contact therewith, this may be readily determined by the intended use of the ice, and the nature of the substrate. In some circumstances, where the chlorine dioxide-containing ice is to be maintained in a freezer chest, with little melting during the course of storage and/or transit, it may be advantageous to have a relatively high level of available $ClO_2$, or available plus releasable $ClO_2$ for marine products (such as fish). In such cases, reliance will be placed mainly on gaseous diffusion of the $ClO_2$ from the chlorine dioxide-containing ice in order to effect the intended microbial reduction or control of the associated product. In other circumstances, such as where melting of the ice will occur, the transformation of the chlorine dioxide-containing ice to the liquid state will release greater amounts of $ClO_2$, as well as quantities of acidified sodium chlorite solution. The latter possesses significant antimicrobial activity, which may well supplement the germicidal effects of the released $ClO_2$. In such cases, therefore, the presence of lower concentrations of $ClO_2$ in the ice may be desirable.

It has also been noted that the $ClO_2$ has a tendency to diffuse out of the chlorine dioxide-containing ice after initial formation, but that such diffusive losses can be minimized by maintaining the chlorine dioxide-containing ice in a sealed environment, which may be accomplished through the use of non-diffusive barriers such as glass or certain impermeable plastic barriers (e.g., Saran, Mylar). Conversely, the chlorine dioxide-containing ice itself, or enclosed in diffusive barrier packages, may serve as a $ClO_2$-releasing source, to disinfect a closed, refrigerated environment, such as for the cold transport of bananas or meat.

The conversation of acidified sodium chlorite to chlorine dioxide, at a fixed pH, and above a certain concentration threshold, appears to be non-linear as the solution in which it is contained is frozen. This is seen in the data shown above in Table 1, where sodium chlorite concentrations of 500, 850 and 1200 ppm gave rise to $ClO_2$ levels in the chlorine dioxide-containing ice of 56.1, 59.5 and 68.4 ppm. On the other hand, when those three compositions are put into contact with a salt solution, the total available plus releasable $ClO_2$ is directly proportional to the sodium chlorite concentration. Below the concentration threshold characteristic of the specific pH, a linearity is observed with respect to sodium chlorite concentration for both $ClO_2$ initially formed in the solution and the ice, and the available plus releasable $ClO_2$ in the presence of saline. This is seen in the following Table 4, covering sodium chlorite concentrations of 62.5 to 250 ppm.

TABLE 4

| | $ClO_2$ in and/or formed by ice | | | | |
|---|---|---|---|---|---|
| Sodium Chlorite Conc'n* | $ClO_2$ in Solution | Water Diluent | Saline Diluent | Increase | % |
| | parts per million (ppm) | | | | |
| 62.5 | 0.11 | 10.1 | 13.5 | 3.4 | 34 |
| 125 | 0.43 | 20.0 | 29.5 | 9.5 | 48 |
| 250 | 0.87 | 30.6 | 52.3 | 21.7 | 71 |

*at pH = 3.0

The amount of metal chlorite in the liquid composition prior to freezing may generally be from about 0.0005% to about 0.5%, typically from about 0.001% to about 0.25%, and preferably from about 0.0025% to about 0.125%. The metal chlorite may be any alkali or alkaline earth chlorite, preferably sodium chlorite or potassium chlorite. The pH's of the aqueous acidified chlorite solutions are generally selected with relation to the metal chlorite concentration, so that the combination will generally produce little free $ClO_2$ upon mixture (e.g., less than about 3 ppm). The pH of the acidified chlorite solution may be generally from about 5.0 to about 1.8, typically from about 4.0 to about 2.0, and preferably from about 2.5 to about 3.5. Any proton-donating acid that is capable of achieving the desired pH may be used, whether inorganic or organic, as well as mixture thereof. Acids which have pKa's greater than about 2, and below about 5, are preferably used in order to provide some reservoir capacity of hydrogen ions following initial consumption of available protons and partial transformation of chlorite ion to chlorous acid. Typical acids include phosphoric, tartaric, citric, malic and acetic.

These acidified chlorite solutions are preferably prepared in cold water, in order to suppress initial $ClO_2$ formation. In general, the utilization of metal chlorite concentration levels at the upper end of the prescribed range requires pH's at the upper end of the prescribed pH range, so as to minimize initial $ClO_2$ formation in the solution prior to freezing. Conversely low concentration of metal chlorite require higher acidities (lower pH's), so that a higher proportion of the chlorite ion will exist as chlorous acid, in order to facilitate $ClO_2$ formation upon freezing. The temperature of freezing should be below about 0° C. (32° F.). When using metal chlorite or acid concentrations at the upper ends of the specified use ranges, there is only slight depression of the normal water freezing temperature. Rapid freezing in small quantities, or as brought about by freezing at temperatures significantly lower below 0° C., may tend to suppress $ClO_2$ formation, since the solution portion of the initially non-frozen matrix may not have sufficient time to react before it too is solidified.

It is also possible, when formulating acidified metal chlorite solutions with low levels of metal chlorite, to effect a more efficient transformation of the metal chlorite to $ClO_2$ by including chloride ion directly in the solution. When preparing the acidified metal chlorite solution by combination of two liquid premixes (i.e., a chlorite and an acid solution), the chloride ion may be included in either of the two liquids. If included in the metal chlorite phase, the pH of that liquid should be above about 10 to minimize any $ClO_2$ generation from the chlorite before acidification. If the acidified metal chlorite solution is to be prepared by addition of an acid concentrate, in liquid or solid form, to a liquid chlorite phase, then that liquid similarly should be above about pH 10. If the acidified metal chlorite solution is to be prepared by a combination of metal chlorite powder and solid or liquid acid concentrate, the appropriate quantity of chloride salt may be included with either material. The chloride salt may be any soluble metal chloride, preferably an alkali or alkaline earth chloride, such as sodium chloride or calcium chloride, respectively. This effect may be seen in the following Table 5 which presents the levels of chlorine dioxide generated from pH 3.5 frozen mixtures of sodium chlorite in which 1% sodium chloride was included. The ice was then dispersed in 3.25% brine solution, and the levels of $ClO_2$ in solution thereafter referred back to the ice basis. For comparison the earlier data obtained from non-chloride containing, pH 3.5 frozen mixtures are provided, with higher sodium chlorite levels than for the chloride-containing solutions.

TABLE 5

| Sodium Chlorite Conc'n* | $ClO_2$ in Solution | $ClO_2$ formed by ice Saline Diluent |
|---|---|---|
| | parts per million (ppm) | |
| 62.5 (+1% NaCl) | <0.1 | 14.6 |
| 125 (+1% NaCl) | <0.1 | 25.2 |
| 250 (+1% NaCl) | <0.1 | 83.9 |
| 500 | <0.1 | 13.5 |
| 850 | <0.1 | 13.1 |
| 1200 | <0.1 | 13.8 |

*at pH = 3.5, prepared from cold premixes

The presence of a significant amount of chloride ion in the frozen acidified chlorite solutions results in a much greater level of $ClO_2$ upon freezing and exposure to brine. It should be noted also that the levels of chlorine dioxide which were present in water solutions, rather than brine, were approximately the same as for the brine solutions, similar to that found in the earlier study. Thus the presence of chloride ion in the mixtures that were frozen caused a greater amount of $ClO_2$ to be formed in the resulting CDC ice, but subsequent exposure of that ice to either water or brine caused no further $ClO_2$ creation. The level of use of the metal chloride salt needed to effect an enhanced generation of $ClO_2$ is generally in the range of about 0.01% to about 5%, preferably from about 0.03% to about 3%.

EXAMPLES

The following examples are presented for purpose of illustration, not limitation.

Example 1

This example describes the preparation of a chlorine dioxide-containing ice ("CDC ice") of the present invention, and the results of exposing fish filets to that ice for a period of ten days, in comparison with the results obtained when similar filets were exposed to normal ice ("control ice"), ice prepared from water at pH 3.0 ("acidified ice"), and ice prepared from diluted "stabilized chlorine dioxide" ("SCD ice"). The comparisons included total aerobic microorganism plate counts (TPCs), at different time periods, as well as $ClO_2$ analysis of the individual ice samples. The fish-filet storage condition were optimized, by appropriate selection of that volume of ice which would allow for near-freezing temperatures during the first 16–18 hours of a 24-hour storage period, and a temperature rise to no grater than 45° F. during the final 6–8 hours of each daily storage period.

Ice Preparation

A solution of 0.05% (500 ppm) sodium chlorite was prepared by dilution of a 30.75% aqueous concentrate, using pre-cooled deionized water. The solution pH was then reduced to 3.0±0.05 with granular citric acid, and the adjusted solution then frozen overnight in one-gallon milk-cartons at −5° to −15° C. to yield the CDC ice of this invention. A similar quantity of control ice was prepared from deionized water, as well as acidified ice prepared from deionized water that had first been reduced to pH 3.0±0.05, using granular citric acid. A further similar quantity of SCD ice was prepared from a solution of 2.0% SCD (equivalent to 2.68% sodium chlorite) by first combining the SCD concentrate with food-grade citric acid crystals at a rate of 16.5 oz. per 1.25 gallons, waiting 5 minutes after the crystals had dissolved and $ClO_2$ had fully generated, and then combining the activated SCD solution concentrate with precooled deionized water at a rate of 1 gallon per 1000 gallons of water. In all cases, the resulting ice was then comminuted in a mechanical ice crusher, and stored in polyethylene bags prior to use.

Fish Preparation

Salmon filets, of uniform size and quality, were obtained from a single wholesale distributor, and washed with deionized water prior to initiation of the study. One filet was selected for each of the 10 days of the study. Each filet was aseptically subdivided into six equal subsections.

Spoilage Study

On "Day 0" four of the "Day 0" subsections were evaluated for TPCs, which had to have been <±0.5 $\log_{10}$ different from one another, to ensure uniformity. Another of the six subsections was held for temperature monitoring throughout the study, immersed in control ice. Subsections of the filets were randomized among the various ice types, which were replenished every 24 hours throughout the study. The filets plus ice were individually placed in covered polystyrene foam cartons, appropriately labeled by sample and length of intended exposure. As the ice melted in each of the cartons, during each day, the filets were maintained at ambient temperatures until the ice was replenished.

Microbiological Evaluation: On each day of the study, just prior to reicing, a sample of standard size was removed from each fish filet subsection with a sterilized coring instrument. Each core was then stored in a separate sterile whirlpak bag, after the addition of 100 ml sterile dilution water. The sample was then vigorously shaken for ~1 minute, and the liquid serially diluted and plated appropriately in order to quantify their microbial loads. The TPCs were then related to "sq. in." of exposed surface from the filet cores from each of the samples from each of the 10 days of storage.

Chemical Evaluation: On Day 0 and each of the test days, samples of the CDC ice were allowed to melt in closed containers and analyzed for oxychlorine ion levels. The ionic chlorine species were quantified on an anion-exchange HPLC column followed by UV absorbance measurement at 214 nM. The $ClO_2$ levels in the CDC ice and SCD ice were determined from solution absorbances at 360 nM and an extinction coefficient of 1242 liter mole$^{-1}$ cm$^{-1}$, on Day 0 samples.

Results

The results of the study are summarized in Table 6. (The level of $ClO_2$ in the 500 ppm CDC ice was 27 ppm, while that for the SCD ice was ~1 ppm.)

TABLE 6

COMPARATIVE DATA ON STORED ICED SALMON FILETS

| ICE SAMPLE | DAY OF STORAGE | | | | | | | | | | |
|---|---|---|---|---|---|---|---|---|---|---|---|
| | 0 | 1 | 2 | 3 | 4 | 5 | 6 | 7 | 8 | 9 | 10 |
| | Total Aerobic Plate Count Reduction ($\log_{10}$ cfu/in$^2$) vs. Control Ice | | | | | | | | | | |
| CDC (500 ppm) ice | — | 1.1 | 0.8 | 2.7 | 2.3 | 2.0 | 3.7 | 5.0 | 5.5 | 4.8 | 2.9 |
| Acidified ice | — | −0.5 | −0.8 | 0.6 | 1.7 | 0.5 | 0.7 | −0.2 | 3.1 | 1.8 | 3.8 |
| SCD ice | — | −0.2 | −0.1 | 0.3 | 1.2 | 0.04 | 0.1 | 0.2 | 1.7 | 0.2 | 2.1 |

This experiment shows significantly reduced surface bacterial counts, as compared with the control filets, over 100,000 times less, per sq in$^2$, by the 7th day of storage. Specifically, the control filets reached a microbial count of 7 $\log_{10}$ cfu/in$^2$ (>10,000,000/in$^2$) in 8 days of storage on the control ice. The filets that were stored on the 500 ppm CDC ice maintained $\log_{10}$ cfu/in$^2$ of 2.3 or less through the entire course of storage, until day 10 when their counts reach a $\log_{10}$ cfu/in$^2$ of 4.6. On a numerical basis, the control fish cfu/in$^2$ were over 12 million by day 8, while on day 8 the 500 ppm filets had a surface population of only 33 cfu/in$^2$. Thus, there is a major advantage provided by the CDC ice as compared with that of the control ice, the acidified ice, and the SCD ice.

Example 2

The above study was also run with a frozen 0.085% (850 ppm) sodium chlorite solution, and all other parameters were identical. (The level of $ClO_2$ in the 850 ppm CDC ice was 40 ppm.) These results were set forth in Table 7.

These fish filets showed TPCs which dropped from $\log_{10}$ 4.13 cfu/in$^2$ (13,500 cfu/in$^2$) on Day 0 to $\log_{10}$ 1.52 cfu/in$^2$ (33 cfu/in$^2$) on Day 3, to $\log_{10}$ 0.52 cfu/in$^2$ (~3 cfu/in$^2$) on Day 6 and thereafter. The control fish, i.e., fish stored on control ice as shown in Example 1, rose from $\log_{10}$ 4.13 cfu/in$^2$ (13,500 cfu/in$^2$) on Day 0 to $\log_{10}$ 7.08 cfu/in$^2$ (>12,000,000 cfu/in$^2$)) on Day 8.

Example 3

The above study also included a frozen 0.12% (1200 ppm) sodium chlorite solution, and all other parameters were identical. These results are presented in Table 8. (The level of $ClO_2$ in the 1200 ppm CDC ice was 76 ppm.)

TABLE 7

COMPARATIVE DATA ON STORED ICED SALMON FILETS

| ICE SAMPLE | DAY OF STORAGE | | | | | | | | | | |
|---|---|---|---|---|---|---|---|---|---|---|---|
| | 0 | 1 | 2 | 3 | 4 | 5 | 6 | 7 | 8 | 9 | 10 |
| | Total Aerobic Plate Count Reduction ($\log_{10}$ cfu/in$^2$) vs. Control Ice | | | | | | | | | | |
| CDC (850 ppm) ice | — | 0.7 | 0.9 | 2.7 | 2.6 | 2.8 | 3.7 | 5.0 | 6.6 | 5.8 | 6.9 |

TABLE 8

| ICE SAMPLE | DAY OF STORAGE | | | | | | | | | | |
|---|---|---|---|---|---|---|---|---|---|---|---|
| | 0 | 1 | 2 | 3 | 4 | 5 | 6 | 7 | 8 | 9 | 10 |
| | Total Aerobic Plate Count Reduction ($\log_{10}$ cfu/in$^2$) vs. Control Ice | | | | | | | | | | |
| CDC (1200 ppm) ice | — | 0.3 | 1.3 | 2.4 | 3.6 | 3.8 | 2.7 | 5.0 | 5.6 | 4.5 | 6.9 |

A comparison of the levels of $ClO_2$ in the CDC ice prepared in Examples 1, 2 and 3 show a relative linearity between initial sodium chlorite concentrations and resulting $ClO_2$ levels as set forth in Table 9.

TABLE 9

$ClO_2$ Levels vs. Initial Chlorite Levels (ppm)

| Acidified Sodium Chlorite Concentration | $ClO_2$ in CDC ice |
|---|---|
| 500 | 27 |
| 850 | 40 |
| 1200 | 76 |

The results of this storage study with 1200 ppm CDC ice are approximately parallel to those of the 850 ppm, with the same approximate TPCs ($\log_{10}$ 0.52 cfu/in$^2$ (~3 cfu/in$^2$) on Day 4, 5, 7, and 10, with slight upwards variations (to a maximum of 66 cfu/in$^2$) on intervening days. In both of the two CDC ice storage studies, the fish filets had approximately 8 million less organisms per sq. in. of surface after 10 days than did fish filets stored on control ice. These differences grew inexorably from the beginning of the study, being about 250–500 times fewer organisms on day 3 upwards to the 10th day, at which point the control fish had become organoleptically unacceptable.

Example 4

This example discloses the preparation of CDC ice for use in suppressing microbial growth on the surfaces of fresh-caught marine fish, as well as controlling the growth of spoilage organisms and extending the shelf life of raw agricultural commodities. A solution of 0.025% sodium chlorite (250 ppm) is adjusted to pH 2.2 with a phosphoric acid buffer, placed in closed 1-gallon plastic containers, then frozen slowly overnight at about 25° F. to optimize the production of $ClO_2$. The ice is then reduced in temperature to about 15° F. prior to removal from the containers and crushing. The crushed CDC ice, containing about 100 ppm of $ClO_2$, is used as a bed for fresh-caught marine fish during transport to land facilities, and during the processing and storing of fresh-picked agricultural produce.

Example 5

This example demonstrates that the level of $ClO_2$ that is produced upon freezing acidified sodium chlorite solutions is significantly dependent upon the rate of freezing—that is, slower freezing allows more time for the concentrated, non-frozen portion of the solution to react and form $ClO_2$. In this experiment, 10 different 1-gallon plastic jugs were filled with a 0.085% solution of sodium chlorite (850 ppm) adjusted to pH 3.0, and slowly frozen over a 2-day period at ~25° F. It was observed that some containers froze at a slower rate consistent with their position in the freezer. After two days each container was thawed completely, and a 2 ml portion of each diluted to 25 ml in water, a portion of which was evaluated spectrophometrically at 360 nM. The results are set forth in Table 10.

TABLE 10

Concentration of $ClO_2$ in Thawed, Slowly-Frozen CDC Ice

| Sample # | ppm | Sample # | ppm |
|---|---|---|---|
| 1 | 187 | 6 | 169 |
| 2 | 171 | 7 | 197 |
| 3 | 160 | 8 | 192 |
| 4 | 176 | 9 | 167 |
| 5 | 136 | 10 | 187 |

The average level of $ClO_2$ was 174 ppm, which is 4.4 times higher than the $ClO_2$ yield from the same concentration solution, at the same pH, of Example 2. In the latter case the liquid was frozen more rapidly, at a lower temperature, with less time for the concentrated solutes to react.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for disinfecting a substrate using a frozen chlorine dioxide containing composition, said method comprising the following steps:
   1) preparing an aqueous solution comprising about 0.0005% to about 0.5% by weight of metal chlorite and a sufficient protic acid concentration to lower the pH of the aqueous solution to a value of about 1.8 to about 5.0, and wherein said prepared aqueous solution has a chlorine dioxide concentration of less than about 3 ppm at all times prior to freezing;
   2) freezing said prepared aqueous solution comprising metal chlorite and protic acid to form a frozen aqueous matrix composition wherein said formed frozen chlorine dioxide containing composition has a chlorine dioxide concentration of more than about 3 ppm; and,
   3) contacting the substrate to be disinfected with a disinfecting amount of said formed frozen chlorine dioxide containing composition.

2. The method of claim 1 wherein the metal chlorite is an alkali or alkaline earth chlorite.

3. The method of claim 1 wherein the metal chlorite is sodium or potassium chlorite.

4. The method of claim 1 wherein the metal chlorite is sodium chlorite.

5. The method of claim 1 wherein the aqueous solution contains metal chlorite at a concentration ranging from 0.001% to 0.25% by weight.

6. The method of claim 1 wherein the aqueous solution contains metal chlorite at a concentration ranging from 0.0025% to 0.125% by weight.

7. The method of claim 1 wherein the protic acid is present in the aqueous solution at a concentration sufficient to lower the pH of the aqueous solution to a value from 2.0 to 4.0.

8. The method of claim 1 wherein the protic acid is present in the aqueous solution at a concentration sufficient to lower the pH of the aqueous solution to a value from 2.5 to 3.5.

9. The method of claim 1 wherein the aqueous solution has a chlorine dioxide concentration less than 2 ppm.

10. The method of claim 1 wherein the aqueous solution has a chlorine dioxide concentration less than 1 ppm.

11. The method of claim 1 wherein the aqueous solution has no detectable level of chlorine dioxide.

12. The method of claim 1 wherein the aqueous solution is formed by mixing an aqueous solution of protic acid and an aqueous solution of metal chlorite, a protic acid in solid form and an aqueous solution of metal chlorite, an aqueous solution of protic acid and a metal chlorite in dry form, or a protic acid in dry form and a metal chlorite in dry form followed by addition of water.

13. The method of claim 1 wherein the protic acid is an organic acid.

14. The method of claim 13 wherein the protic acid is tartaric, citric, malic, acetic, or mixtures thereof.

15. The method of claim 1 wherein the protic acid is an inorganic acid.

16. The method of claim 15 wherein the inorganic acid is phosphoric acid.

17. The method of claim 1 wherein the aqueous solution further comprises a chloride ion.

18. The method of claim 17 wherein the chloride ion is present in the aqueous solution at a concentration ranging from 0.01% to 5%.

19. The method of claim 17 wherein the chloride ion is present in the aqueous solution at a concentration ranging from 0.03% to 3%.

20. The method of claim 17 wherein the source of the chloride ion is a chloride salt.

21. The method of claim 20 wherein the chloride salt is sodium chloride or calcium chloride.

22. The method of claim 1 wherein the substrate is a medical product or organ.

23. The method of claim 1 wherein the substrate is food intended for human or animal consumption.

24. The method of claim 23 wherein the food is a meat product.

25. The method of claim 23 wherein the meat product is beef, fish or poultry.

26. The method of claim 23 wherein the food is a fruit.

27. The method of claim 23 wherein the food is a vegetable.

28. The method of claim 1, further comprising the step of contacting the frozen chlorine dioxide-containing composition with a chloride ion.

29. The method of claim 28 wherein the source of the chloride ion is seawater.

30. The method of claim 28 wherein the source of the chloride ion is brine.

* * * * *